(12) United States Patent
Jennewine

(10) Patent No.: US 8,932,216 B2
(45) Date of Patent: Jan. 13, 2015

(54) METHOD AND SYSTEM FOR PROVIDING DATA MANAGEMENT IN INTEGRATED ANALYTE MONITORING AND INFUSION SYSTEM

(75) Inventor: R. Curtis Jennewine, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1510 days.

(21) Appl. No.: 11/462,982

(22) Filed: Aug. 7, 2006

(65) Prior Publication Data

US 2009/0054745 A1 Feb. 26, 2009

(51) Int. Cl.
  *A61B 5/00* (2006.01)
  *A61B 5/05* (2006.01)
  *G06Q 10/00* (2012.01)
  *G06Q 50/00* (2012.01)
  *A61B 5/145* (2006.01)
  *G06F 19/00* (2011.01)

(52) U.S. Cl.
  CPC ............ *A61B 5/4839* (2013.01); *A61B 5/0031* (2013.01); *A61B 5/14532* (2013.01); *A61B 5/14546* (2013.01); *G06F 19/3468* (2013.01)
  USPC ............... 600/300; 600/301; 600/347; 705/2

(58) Field of Classification Search
  CPC ................... A61B 5/0002; A61B 5/74–5/745; A61B 5/7235–5/7296; A61B 5/14532; A61B 5/1468–5/1495; G06F 19/32–19/366; G06F 19/3406–19/3468; G06Q 50/22–50/24; A61M 1/00; A61M 31/00; G01N 33/48778–33/48792
  See application file for complete search history.

(56) References Cited

U.S. PATENT DOCUMENTS

| | | |
|---|---|---|
| 2,755,036 A | 7/1956 | Mikko |
| 3,923,060 A | 12/1975 | Ellinwood, Jr. |
| 4,003,379 A | 1/1977 | Ellinwood, Jr. |
| 4,055,175 A | 10/1977 | Clemens et al. |
| 4,076,182 A | 2/1978 | Stites |
| 4,151,845 A | 5/1979 | Clemens |
| 4,360,019 A | 11/1982 | Portner |
| 4,387,863 A | 6/1983 | Edmonston |
| 4,441,968 A | 4/1984 | Emmer et al. |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

Diem, P., et al., "Clinical Performance of a Continuous Viscometric Affinity Sensor for Glucose", *Diabetes Technology & Therapeutics*, vol. 6, 2004, pp. 790-799.

(Continued)

*Primary Examiner* — William Thomson
*Assistant Examiner* — Shirley Jian
(74) *Attorney, Agent, or Firm* — Jackson & Co., LLP

(57) ABSTRACT

Methods and systems for providing therapy related data management are provided. The subject systems include one or more device components, and at least one memory storage unit and at least one data storage unit associated with such one or more device components. The device components may include one or more of an analyte monitoring system, a fluid delivery device and a remote terminal. The subject methods include use of the subject systems to optimize treatment of a patient.

7 Claims, 6 Drawing Sheets

(56) References Cited

U.S. PATENT DOCUMENTS

| | | |
|---|---|---|
| 4,464,170 A | 8/1984 | Clemens et al. |
| 4,601,707 A | 7/1986 | Albisser et al. |
| 4,629,145 A | 12/1986 | Graham |
| 4,667,896 A | 5/1987 | Frey et al. |
| 4,685,903 A | 8/1987 | Cable et al. |
| 4,725,010 A | 2/1988 | Lotamer |
| 4,802,638 A | 2/1989 | Burger et al. |
| 4,847,785 A | 7/1989 | Stephens |
| 4,886,505 A | 12/1989 | Haynes et al. |
| 5,019,096 A | 5/1991 | Fox, Jr. et al. |
| 5,051,688 A | 9/1991 | Murase et al. |
| 5,067,665 A | 11/1991 | LoStracco et al. |
| 5,097,834 A | 3/1992 | Skrabal |
| 5,109,577 A | 5/1992 | Young |
| 5,135,004 A | 8/1992 | Adams et al. |
| 5,202,261 A | 4/1993 | Musho et al. |
| 5,209,414 A | 5/1993 | Clemens et al. |
| 5,210,778 A | 5/1993 | Massart |
| 5,228,449 A | 7/1993 | Christ et al. |
| 5,231,988 A | 8/1993 | Wernicke et al. |
| 5,236,143 A | 8/1993 | Dragon |
| 5,237,993 A | 8/1993 | Skrabal |
| 5,250,023 A | 10/1993 | Lee |
| 5,251,126 A | 10/1993 | Kahn et al. |
| 5,266,359 A | 11/1993 | Spielvogel |
| 5,284,425 A | 2/1994 | Holtermann et al. |
| 5,344,411 A | 9/1994 | Domb et al. |
| 5,349,852 A | 9/1994 | Kamen et al. |
| 5,384,547 A | 1/1995 | Lynk et al. |
| 5,390,671 A | 2/1995 | Lord et al. |
| 5,394,877 A | 3/1995 | Orr et al. |
| 5,402,780 A | 4/1995 | Faasse, Jr. |
| 5,410,326 A | 4/1995 | Goldstein |
| 5,437,656 A | 8/1995 | Shikani et al. |
| 5,451,424 A | 9/1995 | Solomon et al. |
| 5,515,390 A | 5/1996 | Benton |
| 5,526,844 A | 6/1996 | Kamen et al. |
| 5,533,389 A | 7/1996 | Kamen et al. |
| 5,552,997 A | 9/1996 | Massart |
| 5,558,640 A | 9/1996 | Pfeiler |
| 5,569,186 A | 10/1996 | Lord et al. |
| 5,593,852 A | 1/1997 | Heller et al. |
| 5,599,321 A | 2/1997 | Conway et al. |
| 5,601,435 A | 2/1997 | Quy |
| 5,609,575 A | 3/1997 | Larson et al. |
| 5,662,904 A | 9/1997 | Ferguson et al. |
| 5,673,691 A | 10/1997 | Abrams et al. |
| 5,726,646 A | 3/1998 | Bane et al. |
| 5,738,220 A | 4/1998 | Geszler |
| 5,748,103 A | 5/1998 | Flach et al. |
| 5,807,375 A | 9/1998 | Gross et al. |
| 5,822,715 A | 10/1998 | Worthington et al. |
| 5,833,603 A | 11/1998 | Kovacs et al. |
| 5,899,855 A | 5/1999 | Brown |
| 5,918,603 A | 7/1999 | Brown |
| 5,925,021 A | 7/1999 | Castellano et al. |
| 5,951,521 A | 9/1999 | Mastrototaro et al. |
| 5,954,643 A | 9/1999 | VanAntwerp et al. |
| 5,956,501 A | 9/1999 | Brown |
| 5,975,120 A | 11/1999 | Novosel |
| 5,987,353 A | 11/1999 | Khatchatrian et al. |
| 5,988,545 A | 11/1999 | King |
| 6,004,278 A | 12/1999 | Botich et al. |
| 6,028,413 A | 2/2000 | Brockmann |
| 6,052,565 A | 4/2000 | Ishikura et al. |
| 6,066,243 A | 5/2000 | Anderson et al. |
| 6,083,248 A | 7/2000 | Thompson |
| 6,091,975 A | 7/2000 | Daddona et al. |
| 6,096,364 A | 8/2000 | Bok et al. |
| 6,129,823 A | 10/2000 | Hughes et al. |
| 6,134,461 A | 10/2000 | Say et al. |
| 6,141,573 A | 10/2000 | Kurnik et al. |
| 6,143,164 A | 11/2000 | Heller et al. |
| 6,175,752 B1 | 1/2001 | Say et al. |
| 6,233,539 B1 | 5/2001 | Brown |
| 6,247,664 B1 | 6/2001 | Petersen et al. |
| 6,248,067 B1 | 6/2001 | Causey et al. |
| 6,254,586 B1 | 7/2001 | Mann et al. |
| 6,270,455 B1 | 8/2001 | Brown |
| 6,284,478 B1 | 9/2001 | Heller et al. |
| 6,314,317 B1 | 11/2001 | Willis |
| 6,359,270 B1 | 3/2002 | Bridson |
| 6,379,301 B1 * | 4/2002 | Worthington et al. ......... 600/300 |
| 6,387,048 B1 | 5/2002 | Schulman et al. |
| 6,418,332 B1 | 7/2002 | Mastrototaro et al. |
| 6,427,088 B1 | 7/2002 | Bowman, IV et al. |
| 6,471,689 B1 * | 10/2002 | Joseph et al. ............... 604/892.1 |
| 6,482,156 B2 | 11/2002 | Iliff |
| 6,484,045 B1 | 11/2002 | Holker et al. |
| 6,485,461 B1 | 11/2002 | Mason et al. |
| 6,493,069 B1 | 12/2002 | Nagashimada et al. |
| 6,498,043 B1 | 12/2002 | Schulman et al. |
| 6,544,212 B2 * | 4/2003 | Galley et al. ..................... 604/31 |
| 6,546,268 B1 | 4/2003 | Ishikawa et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,576,101 B1 | 6/2003 | Heller et al. |
| 6,577,899 B2 | 6/2003 | Lebel et al. |
| 6,585,644 B2 | 7/2003 | Lebel et al. |
| 6,598,824 B2 | 7/2003 | Schmidt |
| 6,635,014 B2 | 10/2003 | Starkweather et al. |
| 6,641,533 B2 | 11/2003 | Causey, III et al. |
| 6,641,562 B1 | 11/2003 | Peterson |
| 6,648,821 B2 | 11/2003 | Lebel et al. |
| 6,656,114 B1 | 12/2003 | Poulsen et al. |
| 6,656,158 B2 | 12/2003 | Gregory et al. |
| 6,656,159 B2 | 12/2003 | Flaherty |
| 6,658,396 B1 | 12/2003 | Tang et al. |
| 6,659,948 B2 | 12/2003 | Lebel et al. |
| 6,668,196 B1 | 12/2003 | Villegas et al. |
| 6,669,669 B2 | 12/2003 | Flaherty et al. |
| 6,676,816 B2 | 1/2004 | Mao et al. |
| 6,687,546 B2 | 2/2004 | Lebel et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,733,446 B2 | 5/2004 | Lebel et al. |
| 6,736,797 B1 | 5/2004 | Larsen et al. |
| 6,740,059 B2 | 5/2004 | Flaherty |
| 6,740,075 B2 | 5/2004 | Lebel et al. |
| 6,741,877 B1 | 5/2004 | Shults et al. |
| 6,744,350 B2 | 6/2004 | Blomquist |
| 6,749,587 B2 | 6/2004 | Flaherty |
| 6,758,810 B2 | 7/2004 | Lebel et al. |
| 6,768,425 B2 | 7/2004 | Flaherty et al. |
| 6,789,195 B1 | 9/2004 | Prihoda et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,558 B2 | 12/2004 | Flaherty et al. |
| 6,837,858 B2 | 1/2005 | Cunningham et al. |
| 6,850,790 B2 | 2/2005 | Berner et al. |
| 6,852,104 B2 | 2/2005 | Blomquist |
| 6,862,465 B2 | 3/2005 | Shults et al. |
| 6,873,268 B2 | 3/2005 | Lebel et al. |
| 6,882,940 B2 | 4/2005 | Potts et al. |
| 6,887,270 B2 | 5/2005 | Miller et al. |
| 6,896,666 B2 | 5/2005 | Kochamba et al. |
| 6,902,207 B2 | 6/2005 | Lickliter |
| 6,916,159 B2 | 7/2005 | Rush et al. |
| 6,923,763 B1 | 8/2005 | Kovatchev et al. |
| 6,931,327 B2 | 8/2005 | Goode, Jr. et al. |
| 6,936,006 B2 | 8/2005 | Sabra |
| 6,946,446 B2 | 9/2005 | Ma et al. |
| 6,950,708 B2 | 9/2005 | Bowman IV et al. |
| 6,958,705 B2 | 10/2005 | Lebel et al. |

(56) References Cited

U.S. PATENT DOCUMENTS

| | | | |
|---|---|---|---|
| 6,960,192 B1 | 11/2005 | Flaherty et al. |
| 6,974,437 B2 | 12/2005 | Lebel et al. |
| 6,999,854 B2 * | 2/2006 | Roth ........................... 700/282 |
| 7,003,336 B2 | 2/2006 | Holker et al. |
| 7,015,817 B2 | 3/2006 | Copley et al. |
| 7,016,713 B2 | 3/2006 | Gardner et al. |
| 7,018,360 B2 | 3/2006 | Flaherty et al. |
| 7,024,245 B2 | 4/2006 | Lebel et al. |
| 7,027,848 B2 | 4/2006 | Robinson et al. |
| 7,027,931 B1 | 4/2006 | Jones et al. |
| 7,029,455 B2 | 4/2006 | Flaherty |
| 7,034,677 B2 | 4/2006 | Steinthal et al. |
| 7,041,468 B2 * | 5/2006 | Drucker et al. ................. 435/14 |
| 7,046,153 B2 | 5/2006 | Oja et al. |
| 7,052,251 B2 | 5/2006 | Nason et al. |
| 7,052,472 B1 | 5/2006 | Miller et al. |
| 7,066,922 B2 | 6/2006 | Angel et al. |
| 7,074,307 B2 | 7/2006 | Simpson et al. |
| 7,077,328 B2 | 7/2006 | Krishnaswamy et al. |
| 7,079,977 B2 | 7/2006 | Osorio et al. |
| 7,081,195 B2 | 7/2006 | Simpson et al. |
| 7,092,891 B2 | 8/2006 | Maus et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,133,717 B2 | 11/2006 | Coston et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,144,384 B2 | 12/2006 | Gorman et al. |
| 7,153,265 B2 | 12/2006 | Vachon |
| 7,155,112 B2 | 12/2006 | Uno et al. |
| 7,155,290 B2 | 12/2006 | Von Arx et al. |
| 7,167,818 B2 | 1/2007 | Brown |
| 7,171,274 B2 | 1/2007 | Starkweather et al. |
| 7,171,312 B2 | 1/2007 | Steinthal et al. |
| 7,179,226 B2 * | 2/2007 | Crothall et al. ............... 600/300 |
| 7,192,450 B2 | 3/2007 | Brauker et al. |
| 7,207,974 B2 | 4/2007 | Safabash et al. |
| 7,216,665 B1 | 5/2007 | Sims, Jr. |
| 7,226,278 B2 | 6/2007 | Nason et al. |
| 7,226,442 B2 | 6/2007 | Sheppard et al. |
| 7,226,978 B2 | 6/2007 | Tapsak et al. |
| 7,229,042 B2 | 6/2007 | Thebault et al. |
| 7,267,665 B2 | 9/2007 | Steil et al. |
| 7,276,029 B2 | 10/2007 | Goode, Jr. et al. |
| 7,286,894 B1 | 10/2007 | Grant et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,354,420 B2 | 4/2008 | Steil et al. |
| 7,364,568 B2 | 4/2008 | Angel et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,483,736 B2 | 1/2009 | Marchitto et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,547,281 B2 | 6/2009 | Hayes et al. |
| 7,583,990 B2 | 9/2009 | Goode, Jr. et al. |
| 7,591,801 B2 * | 9/2009 | Brauker et al. ............... 604/161 |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,630,748 B2 | 12/2009 | Budiman |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,645,263 B2 | 1/2010 | Angel et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,697,967 B2 | 4/2010 | Stafford |
| 7,699,775 B2 | 4/2010 | Desai et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,310 B2 | 6/2010 | Taub et al. |
| 7,736,344 B2 | 6/2010 | Moberg et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,783,333 B2 | 8/2010 | Brister et al. |
| 7,792,562 B2 | 9/2010 | Shults et al. |
| 7,811,231 B2 | 10/2010 | Jin et al. |
| 7,822,454 B1 | 10/2010 | Alden et al. |
| 7,826,981 B2 | 11/2010 | Goode, Jr. et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,914,450 B2 | 3/2011 | Goode, Jr. et al. |
| 7,938,797 B2 | 5/2011 | Estes |
| 7,941,200 B2 * | 5/2011 | Weinert et al. ................. 600/347 |
| 7,946,985 B2 | 5/2011 | Mastrototaro et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 8,010,174 B2 | 8/2011 | Goode et al. |
| 8,010,256 B2 | 8/2011 | Oowada |
| 8,085,151 B2 | 12/2011 | Jennewine |
| 8,192,394 B2 | 6/2012 | Estes et al. |
| 8,216,138 B1 | 7/2012 | McGarraugh et al. |
| 8,282,549 B2 * | 10/2012 | Brauker et al. ............... 600/365 |
| 8,461,985 B2 | 6/2013 | Fennell et al. |
| 8,597,570 B2 * | 12/2013 | Terashima et al. ........... 422/68.1 |
| 2001/0020124 A1 | 9/2001 | Tamada |
| 2001/0037366 A1 | 11/2001 | Webb et al. |
| 2001/0047604 A1 | 12/2001 | Valiulis |
| 2002/0016719 A1 | 2/2002 | Nemeth et al. |
| 2002/0019612 A1 | 2/2002 | Watanabe et al. |
| 2002/0054320 A1 | 5/2002 | Ogino |
| 2002/0095076 A1 | 7/2002 | Krausman et al. |
| 2002/0106709 A1 | 8/2002 | Potts et al. |
| 2002/0107476 A1 | 8/2002 | Mann et al. |
| 2002/0133107 A1 | 9/2002 | Darcey |
| 2002/0147135 A1 | 10/2002 | Schnell |
| 2002/0169439 A1 | 11/2002 | Flaherty et al. |
| 2002/0169635 A1 | 11/2002 | Shillingburg |
| 2002/0193679 A1 | 12/2002 | Malave et al. |
| 2003/0021729 A1 | 1/2003 | Moller et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0055380 A1 | 3/2003 | Flaherty et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069541 A1 | 4/2003 | Gillis et al. |
| 2003/0073414 A1 | 4/2003 | P. Capps |
| 2003/0100040 A1 | 5/2003 | Bonnecaze et al. |
| 2003/0114836 A1 | 6/2003 | Estes et al. |
| 2003/0114897 A1 | 6/2003 | Von Arx et al. |
| 2003/0122021 A1 | 7/2003 | McConnell et al. |

(56) References Cited

U.S. PATENT DOCUMENTS

| | | |
|---|---|---|
| 2003/0144362 A1 | 7/2003 | Utterberg et al. |
| 2003/0147515 A1 | 8/2003 | Kai et al. |
| 2003/0167035 A1 | 9/2003 | Flaherty et al. |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0041749 A1 | 3/2004 | Dixon |
| 2004/0045879 A1 | 3/2004 | Shults et al. |
| 2004/0063435 A1 | 4/2004 | Sakamoto et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0122530 A1 | 6/2004 | Hansen et al. |
| 2004/0133390 A1 | 7/2004 | Osorio et al. |
| 2004/0135684 A1 | 7/2004 | Steinthal et al. |
| 2004/0147872 A1 | 7/2004 | Thompson |
| 2004/0152622 A1 | 8/2004 | Keith et al. |
| 2004/0153032 A1 | 8/2004 | Garribotto et al. |
| 2004/0155770 A1 | 8/2004 | Nelson et al. |
| 2004/0162521 A1 | 8/2004 | Bengtsson |
| 2004/0167464 A1 | 8/2004 | Ireland et al. |
| 2004/0186362 A1 | 9/2004 | Brauker et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0204868 A1 | 10/2004 | Maynard et al. |
| 2004/0210180 A1 | 10/2004 | Altman |
| 2004/0210208 A1 | 10/2004 | Paul et al. |
| 2004/0225338 A1 | 11/2004 | Lebel et al. |
| 2004/0254433 A1 | 12/2004 | Bandis et al. |
| 2004/0260478 A1 | 12/2004 | Schwamm |
| 2005/0001024 A1 | 1/2005 | Kusaka et al. |
| 2005/0004439 A1 | 1/2005 | Shin et al. |
| 2005/0010269 A1 | 1/2005 | Lebel et al. |
| 2005/0027180 A1 | 2/2005 | Goode, Jr. et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0043598 A1 | 2/2005 | Goode, Jr. et al. |
| 2005/0049179 A1 | 3/2005 | Davidson et al. |
| 2005/0065464 A1 | 3/2005 | Talbot et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0112169 A1 | 5/2005 | Brauker et al. |
| 2005/0113653 A1 | 5/2005 | Fox et al. |
| 2005/0113886 A1 | 5/2005 | Fischell et al. |
| 2005/0116683 A1 | 6/2005 | Cheng et al. |
| 2005/0119540 A1 | 6/2005 | Potts et al. |
| 2005/0137530 A1 | 6/2005 | Campbell et al. |
| 2005/0143635 A1 | 6/2005 | Kamath et al. |
| 2005/0171512 A1 | 8/2005 | Flaherty |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0187442 A1 | 8/2005 | Cho et al. |
| 2005/0187720 A1 | 8/2005 | Goode, Jr. et al. |
| 2005/0192557 A1* | 9/2005 | Brauker et al. ............... 604/503 |
| 2005/0195930 A1 | 9/2005 | Spital et al. |
| 2005/0203360 A1 | 9/2005 | Brauker et al. |
| 2005/0203461 A1 | 9/2005 | Flaherty et al. |
| 2005/0204134 A1 | 9/2005 | Von Arx et al. |
| 2005/0214892 A1 | 9/2005 | Kovatchev et al. |
| 2005/0238507 A1 | 10/2005 | DiIanni et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0261667 A1 | 11/2005 | Crank et al. |
| 2005/0277872 A1 | 12/2005 | Colby et al. |
| 2005/0277912 A1 | 12/2005 | John |
| 2006/0001551 A1 | 1/2006 | Kraft et al. |
| 2006/0004603 A1 | 1/2006 | Peterka et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0065772 A1 | 3/2006 | Grant et al. |
| 2006/0079740 A1 | 4/2006 | Silver et al. |
| 2006/0091006 A1 | 5/2006 | Wang et al. |
| 2006/0095020 A1 | 5/2006 | Casas et al. |
| 2006/0142651 A1 | 6/2006 | Brister et al. |
| 2006/0154642 A1 | 7/2006 | Scannell |
| 2006/0166629 A1 | 7/2006 | Reggiardo |
| 2006/0173406 A1 | 8/2006 | Hayes et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0247508 A1 | 11/2006 | Fennell |
| 2006/0258929 A1 | 11/2006 | Goode et al. |
| 2006/0272652 A1 | 12/2006 | Stocker et al. |
| 2006/0282290 A1 | 12/2006 | Flaherty et al. |
| 2006/0290496 A1 | 12/2006 | Peeters et al. |
| 2006/0293577 A1 | 12/2006 | Morrison et al. |
| 2006/0293607 A1 | 12/2006 | Alt et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032717 A1 | 2/2007 | Brister et al. |
| 2007/0033074 A1 | 2/2007 | Nitzan et al. |
| 2007/0060869 A1* | 3/2007 | Tolle et al. ............... 604/65 |
| 2007/0060870 A1 | 3/2007 | Tolle et al. |
| 2007/0060871 A1 | 3/2007 | Istoc et al. |
| 2007/0060979 A1 | 3/2007 | Strother et al. |
| 2007/0066956 A1 | 3/2007 | Finkel |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zivitz et al. |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0128682 A1 | 6/2007 | Rosman et al. |
| 2007/0129621 A1 | 6/2007 | Kellogg et al. |
| 2007/0149875 A1 | 6/2007 | Ouyang et al. |
| 2007/0163880 A1 | 7/2007 | Woo et al. |
| 2007/0191702 A1 | 8/2007 | Yodfat et al. |
| 2007/0203407 A1 | 8/2007 | Hoss et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219480 A1 | 9/2007 | Kamen et al. |

(56) References Cited

U.S. PATENT DOCUMENTS

| | | |
|---|---|---|
| 2007/0219597 A1 | 9/2007 | Kamen et al. |
| 2007/0228071 A1 | 10/2007 | Kamen et al. |
| 2007/0235331 A1 | 10/2007 | Simpson et al. |
| 2007/0249922 A1 | 10/2007 | Peyser et al. |
| 2007/0255114 A1 | 11/2007 | Ackermann et al. |
| 2007/0255321 A1 | 11/2007 | Gerber et al. |
| 2007/0255348 A1 | 11/2007 | Holtzclaw |
| 2007/0282299 A1 | 12/2007 | Hellwig |
| 2007/0299409 A1 | 12/2007 | Whitbourne et al. |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0018480 A1 | 1/2008 | Sham |
| 2008/0021436 A1 | 1/2008 | Wolpert et al. |
| 2008/0021666 A1 | 1/2008 | Goode, Jr. et al. |
| 2008/0033254 A1 | 2/2008 | Kamath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0093447 A1 | 4/2008 | Johnson et al. |
| 2008/0097246 A1 | 4/2008 | Stafford |
| 2008/0108942 A1 | 5/2008 | Brister et al. |
| 2008/0114228 A1 | 5/2008 | McCluskey et al. |
| 2008/0119707 A1 | 5/2008 | Stafford |
| 2008/0139910 A1 | 6/2008 | Mastrototaro et al. |
| 2008/0177149 A1 | 7/2008 | Weinert et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0262469 A1 | 10/2008 | Brister et al. |
| 2008/0269687 A1 | 10/2008 | Chong et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0319085 A1 | 12/2008 | Wright et al. |
| 2009/0005666 A1 | 1/2009 | Shin et al. |
| 2009/0006133 A1 | 1/2009 | Weinert et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054747 A1 | 2/2009 | Fennell |
| 2009/0054748 A1 | 2/2009 | Feldman et al. |
| 2009/0062633 A1 | 3/2009 | Brauker et al. |
| 2009/0062635 A1 | 3/2009 | Brauker et al. |
| 2009/0069650 A1 | 3/2009 | Jennewine et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085873 A1 | 4/2009 | Betts et al. |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105560 A1 | 4/2009 | Solomon |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1* | 6/2009 | Peyser et al. .................. 604/66 |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0292188 A1 | 11/2009 | Hoss et al. |

(56) References Cited

U.S. PATENT DOCUMENTS

| | | |
|---|---|---|
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0174157 A1 | 7/2010 | Brister et al. |
| 2010/0174266 A1 | 7/2010 | Estes |
| 2010/0185069 A1 | 7/2010 | Brister et al. |
| 2010/0185175 A1 | 7/2010 | Kamen et al. |
| 2010/0191082 A1 | 7/2010 | Brister et al. |
| 2010/0198142 A1 | 8/2010 | Sloan et al. |
| 2010/0213080 A1 | 8/2010 | Celentano et al. |
| 2010/0217105 A1 | 8/2010 | Yodfat et al. |
| 2010/0240975 A1 | 9/2010 | Goode et al. |
| 2010/0262201 A1 | 10/2010 | He et al. |
| 2010/0274111 A1 | 10/2010 | Say et al. |
| 2010/0292634 A1 | 11/2010 | Kircher et al. |
| 2010/0312176 A1 | 12/2010 | Lauer et al. |
| 2010/0313105 A1 | 12/2010 | Nekoomaram et al. |
| 2010/0331642 A1 | 12/2010 | Bruce et al. |
| 2011/0031986 A1 | 2/2011 | Bhat et al. |
| 2011/0040256 A1 | 2/2011 | Bobroff et al. |
| 2011/0077490 A1 | 3/2011 | Simpson et al. |
| 2011/0148905 A1 | 6/2011 | Simmons et al. |
| 2011/0178461 A1 | 7/2011 | Chong et al. |
| 2011/0208027 A1 | 8/2011 | Wagner et al. |
| 2011/0257895 A1 | 10/2011 | Brauker et al. |
| 2011/0287528 A1 | 11/2011 | Fern et al. |
| 2012/0165640 A1 | 6/2012 | Galley et al. |
| 2013/0235166 A1 | 9/2013 | Jones et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| EP | 1956371 | 8/2008 |
| EP | 2260757 | 12/2010 |
| WO | WO-00/74753 | 12/2000 |
| WO | WO-01/52935 | 7/2001 |
| WO | WO-01/54753 | 8/2001 |
| WO | WO-02/39086 | 5/2002 |
| WO | WO-03/006091 | 1/2003 |
| WO | WO-03/090509 | 4/2003 |
| WO | WO-03/053503 | 7/2003 |
| WO | WO-03/071930 | 9/2003 |
| WO | WO-03/103763 | 12/2003 |
| WO | WO-2004/015539 | 2/2004 |
| WO | WO-2006/037109 | 4/2006 |
| WO | WO-2007/065285 | 6/2007 |
| WO | WO-2007/101260 | 9/2007 |
| WO | WO-2007/149319 | 12/2007 |
| WO | WO-2008/001366 | 1/2008 |
| WO | WO-2008/003003 | 1/2008 |
| WO | WO-2008/005780 | 1/2008 |
| WO | WO-2008/086541 | 7/2008 |
| WO | WO-2011/104616 | 9/2011 |

OTHER PUBLICATIONS

Garg, S., et al., "Improvement in Glycemic Excursions with a Transcutaneous, Real-Time Continuous Glucose Sensor", *Diabetes Care*, vol. 29, No. 1, 2006, pp. 44-50.

Kondepati, V., et al., "Recent Progress in Analytical Instrumentation for Glycemic Control in Diabetic and Critically Ill Patients", *Analytical Bioanalytical Chemistry*, vol. 388, 2007, pp. 545-563.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Parker, R., et al., "Robust H∞ Glucose Control in Diabetes Using a Physiological Model", *AIChE Journal*, vol. 46, No. 12, 2000, pp. 2537-2549.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Li, Y., et al., "In Vivo Release From a Drug Delivery MEMS Device", *Journal of Controlled Release*, vol. 100, 2004, 99. 211-219.

Panteleon, A. E., et al., "The Role of the Independent Variable to Glucose Sensor Calibration", *Diabetes Technology & Therapeutics*, vol. 5, No. 3, 2003, pp. 401-410.

* cited by examiner

US 8,932,216 B2

METHOD AND SYSTEM FOR PROVIDING DATA MANAGEMENT IN INTEGRATED ANALYTE MONITORING AND INFUSION SYSTEM

BACKGROUND

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

The external infusion devices are typically connected to an infusion set which includes a cannula that is placed transcutaneously through the skin of the patient to infuse a select dosage of insulin based on the infusion device's programmed basal rates or any other infusion rates as prescribed by the patient's doctor. Generally, the patient is able to control the pump to administer additional doses of insulin during the course of wearing and operating the infusion device such as for, administering a carbohydrate bolus prior to a meal. Certain infusion devices include food database that has associated therewith, an amount of carbohydrate, so that the patient may better estimate the level of insulin dosage needed for, for example, calculating a bolus amount.

However, in general, most estimation or calculation of a bolus amount for administration, or a determination of a suitable basal profile, for that matter, are educated estimates based on the patient's physiology as determined by the patient's doctor, or an estimate performed by the patient. Moreover, the infusion devices do not generally include enhancement features that would better assist the diabetic patients to control and/or manage the glucose levels.

In view of the foregoing, it would be desirable to have an approach to provide methods and system for data processing associated with a patient's monitored analyte levels for providing semi automatic or automatic recommendation based on the processed data such as, for example, therapy profile, glucose level pattern recognition, and the like.

SUMMARY OF THE INVENTION

In accordance with one embodiment of the present invention, there is provided method and system for detecting a predetermined rate of increase in an analyte level of a patient over a predefined time period, and associating a temporal identifier associated with the detected predetermined rate of increase in the analyte level of the patient.

These and other objects, features and advantages of the present invention will become more fully apparent from the following detailed description of the embodiments, the appended claims and the accompanying drawings.

DETAILED DESCRIPTION

Figure 1:
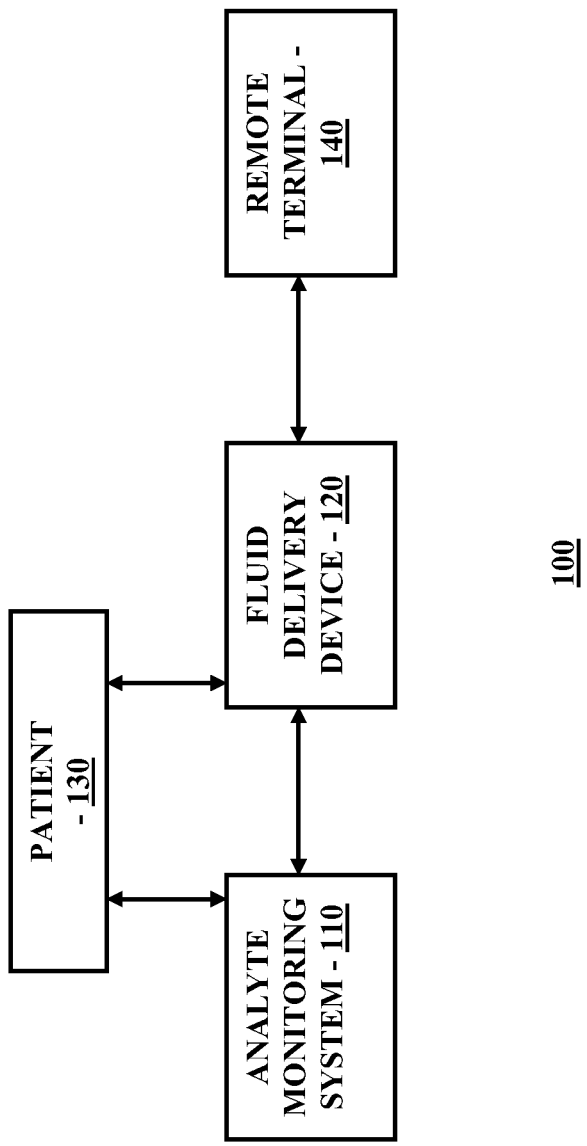
FIG. 1 is a block diagram illustrating a therapy management system for practicing one embodiment of the present invention.

FIG. 1 is a block diagram illustrating an insulin therapy management system for practicing one embodiment of the present invention. Referring to FIG. 1, the therapy management system 100 includes an analyte monitoring system 110 operatively coupled to a fluid delivery device 120, which may be in turn, operatively coupled to a remote terminal 140. As shown the Figure, the analyte monitoring system 110 is, in one embodiment, coupled to the patient 130 so as to monitor or measure the analyte levels of the patient. Moreover, the fluid delivery device 120 is coupled to the patient using, for example, an infusion set and tubing connected to a cannula (not shown) that is placed transcutaneously through the skin of the patient so as to infuse medication such as, for example, insulin, to the patient.

Referring to FIG. 1, in one embodiment the analyte monitoring system 110 in one embodiment may include one or more analyte sensors subcutaneously positioned such that at least a portion of the analyte sensors are maintained in fluid contact with the patient's analytes. The analyte sensors may include, but not limited to short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the fluid delivery device and/or the remote terminal 140 for further data processing and analysis.

The transmitter units of the analyte monitoring system 110 may be, in one embodiment, configured to transmit the analyte related data substantially in real time to the fluid delivery device 120 and/or the remote terminal 140 after receiving it from the corresponding analyte sensors such that the analyte level such as glucose level of the patient 130 may be monitored in real time. In one aspect, the analyte levels of the patient may be obtained using one or more of discrete blood glucose testing devices such as blood glucose meters, or continuous analyte monitoring systems such as continuous glucose monitoring systems.

Additional analytes that may be monitored, determined or detected the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present invention, the transmitter units of the analyte monitoring system 110 may be configured to directly communicate with one or more of the remote terminal 140 or the fluid delivery device 120. Furthermore, within the scope of the present invention, additional devices may be provided for communication in the therapy management system 100 including additional receiver/data processing unit, remote terminals (such as a physician's terminal and/or a bedside terminal in a hospital environment, for example. In addition, within the scope of the present invention, one or more of the analyte monitoring system 110, the fluid delivery device 120 and the remote terminal 140 may be configured to communicate over a wireless data communication link such as, but not limited to RF communication link, Bluetooth® communication link, infrared communication link, or any other type of suitable wireless communication connection between two or more electronic devices, which may further be uni-directional or bi-directional communication between the two or more devices. Alternatively, the data communication link may include wired cable connection such as, for example, but not limited to RS232 connection, USB connection, or serial cable connection.

The fluid delivery device 120 may include in one embodiment, but not limited to, an external infusion device such as an external insulin infusion pump, an implantable pump, a pen-type insulin injector device, a patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Referring back to FIG. 1, in one embodiment, the analyte monitoring system 110 includes a strip port configured to receive a test strip for capillary blood glucose testing. In one aspect, the glucose level measured using the test strip may, in addition, be configured to provide periodic calibration of the analyte sensors of the analyte monitoring system 110 to assure and improve the accuracy of the analyte levels detected by the analyte sensors.

Figure 2:
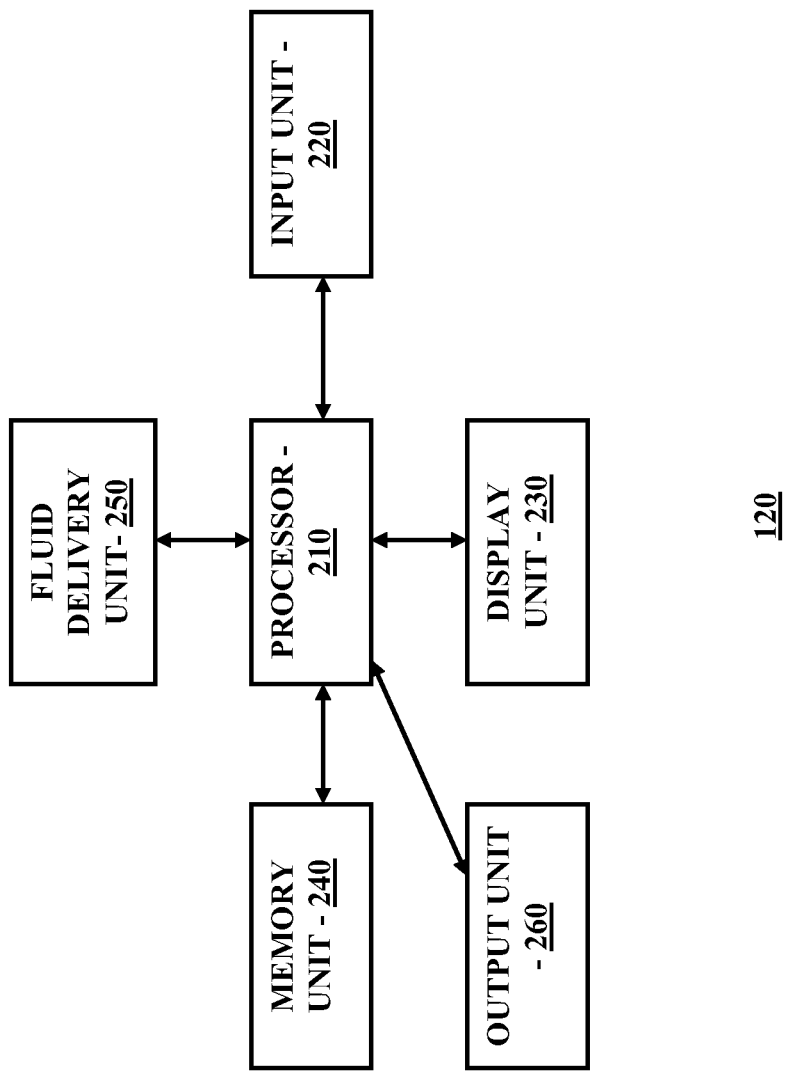
FIG. 2 is a block diagram of a fluid delivery device of FIG. 1 in one embodiment of the present invention.

FIG. 2 is a block diagram of a fluid delivery device of FIG. 1 in one embodiment of the present invention. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as safety measure and to provide redundancy in case of a single processor failure. Moreover, processing capabilities may be shared between multiple processor units within the fluid delivery device 120 such that pump functions and/or control may be performed faster and more accurately.

Referring back to FIG. 2, the input unit 220 operatively coupled to the processor 210 may include a jog dial, key pad buttons, a touch pad screen, or any other suitable input mechanism for providing input commands to the fluid delivery device 120. More specifically, in the case of a jog dial input device, or a touch pad screen, for example, the patient or user of the fluid delivery device 120 will manipulate the respective jog dial or touch pad in conjunction with the display unit 230 which performs as both a data input and output units. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include an audible alarm including one or more tones and//or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that is configured to store data as well as program instructions for access by the processor 210 and execution to control the fluid delivery device 120 and/or to perform data processing based on data received from the analyte monitoring system 110, the remote terminal 140, the patient 130 or any other data input source.

Within the scope of the present invention, the fluid delivery device 120 may be configured to ascertain these consecutive glucose readings from the data stream received from the analyte monitoring system 110. Moreover, the predefined time period may additionally include any other suitable time period where the monitored analyte levels may provide information associated with the patient's physiological condition as pertains to the insulin therapy and diabetes management. For example, the predefined time period may include a 4-7 day period (or longer or shorter as may be appropriate), where the fluid delivery device 120 may be configured to receive the glucose readings at a specific time of the day (for example, at 7 am in the morning). In this case, the consecutive glucose readings may include each measured glucose level at 7 am in the morning for the 4-7 day period.

Figure 3:
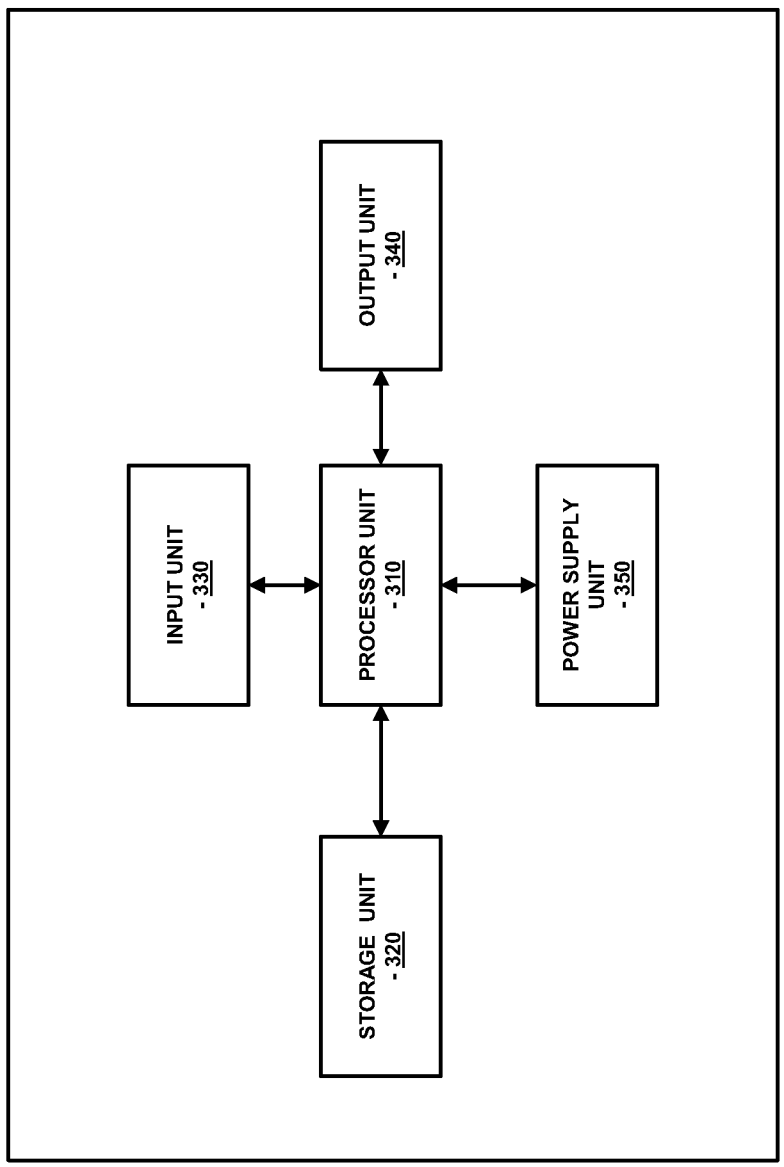
FIG. 3 is a block diagram illustrating the remote terminal of FIG. 1 for performing data processing in accordance with one embodiment of the present invention.

FIG. 3 is a block diagram illustrating the remote terminal of FIG. 1 for performing data processing in accordance with one embodiment of the present invention. Referring to FIG. 3, the remote terminal 140 in one embodiment includes a processor unit 310 operatively coupled to a storage unit 320. The storage unit 320 in one embodiment includes one or more of a volatile memory and non-volatile memory for storing, for example, program instructions associated with the operation of the remote terminal 140 for execution by the processor unit 310, and further, for storing analyte related data as well as infusion related data.

Referring back to FIG. 3, the processor unit 310 is further operatively coupled to an input unit 330, and an output unit 340, as well as a power supply unit 350. In one embodiment, the power supply unit 350 is configured to provide power to each of the components of the remote terminal 140 described above, and further, to effectively manage power based on instructions received from the processor unit 310. The input unit 330 may be configured to receive one or more instructions, commands or data from a patient via, for example, a keyboard device, a mouse device, or any other similar type of input devices, and for providing the received one or more instructions, commands or information, to the processor unit 310 for further processing and control.

Additionally, the output unit 340 in one embodiment is configured to output one or more data or information under the control of the processor unit 310. For example, in one embodiment, the output unit 340 may include a visual output unit such as a display unit, an audio output unit, such as a speaker unit, or a tactile output unit, such as a vibratory unit. In one embodiment, one two or more of such output components may be combined to either sequentially or simultaneously output the corresponding output signals under the command and control of the processor unit 310.

Figure 4:
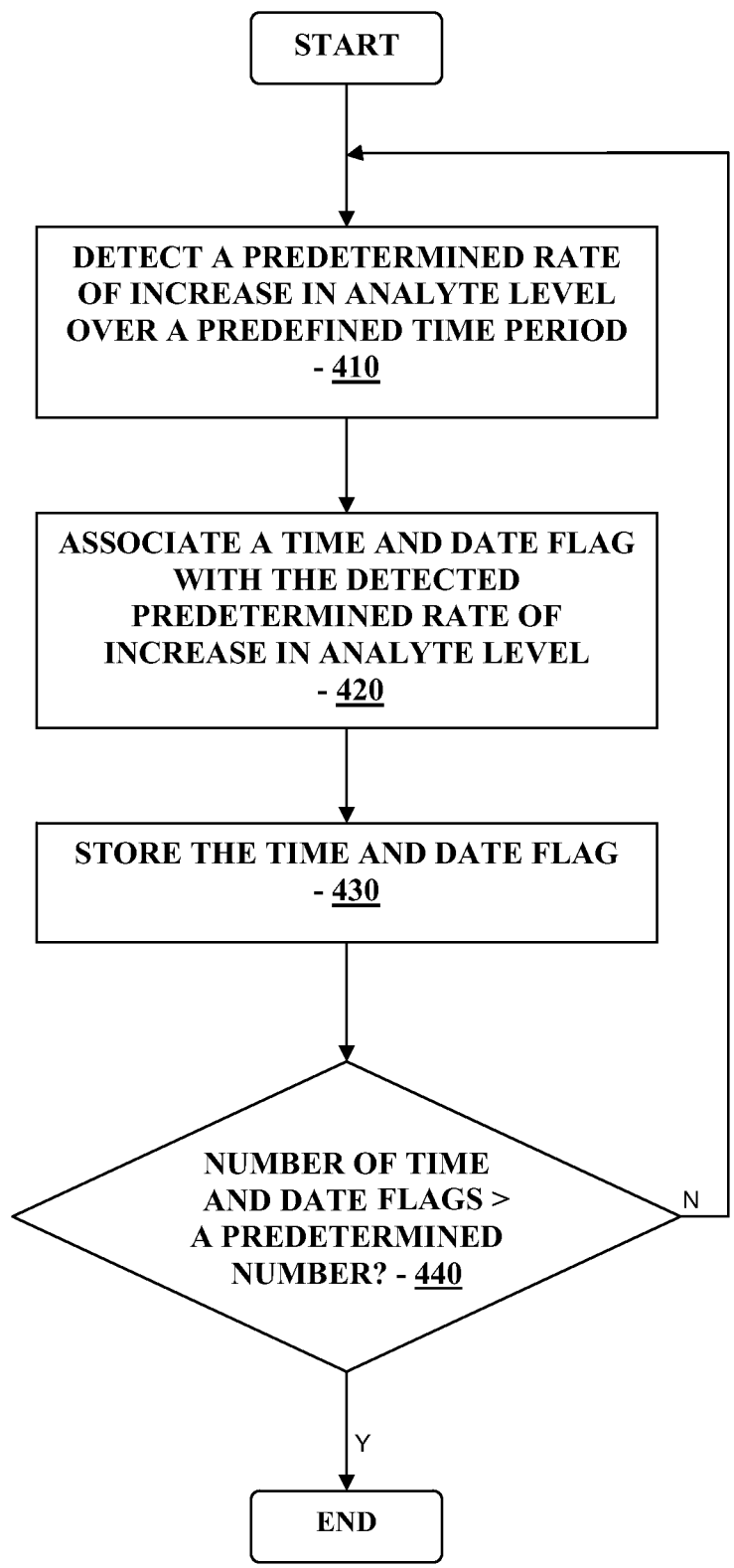
FIG. 4 is a flowchart illustrating analyte level associated data processing related to meals in accordance with one embodiment of the present invention.

FIG. 4 is a flowchart illustrating analyte level associated data processing related to meals in accordance with one embodiment of the present invention. Referring to FIG. 4, a predetermined rate of increase in analyte level over a predefined time period is detected (410). For example, the rate of increase in the analyte level may be predefined or preprogrammed in the processor unit 310 (FIG. 3) to correspond or correlate to a meal event. That is, in the event that a rapid peak or sudden spike is detected in the monitored analyte level, the processor unit 310 is configured to associate such event with a predefined meal event.

Referring back to FIG. 4, thereafter, the detected predetermined rate of increase in analyte level is associated with a time and date flag (420). Then, the associated time and date flag is stored in a memory (430), for example in the storage unit 320 (FIG. 3). It is then determined whether the number of the time and date flags is greater than a predetermined number (440). That is, in one embodiment, it is determined whether the number of time and date flags associated with each associated predetermined rate of increase in monitored analyte levels exceeds a predetermined number. In one embodiment, the number of time and date flags is associated with the number of meals that the patient ingests during a predetermined time period. That is, in one embodiment, each rapid increase in the analyte level is associated with a meal event of the patient.

In this manner, in one embodiment, each meal event of the patient may be associated with a time and date flag and stored in a database with an associated glucose level. Accordingly, based on the monitored analyte levels, in one embodiment, each meal event may be lined up for further processing without the need for the patient to individually lineup each meal event. That is, in one embodiment of the present invention, meal related pattern recognition may be performed and executed automatically without the manual data association by the patient for each meal time and date information and the associated carbohydrate information.

Figure 5:
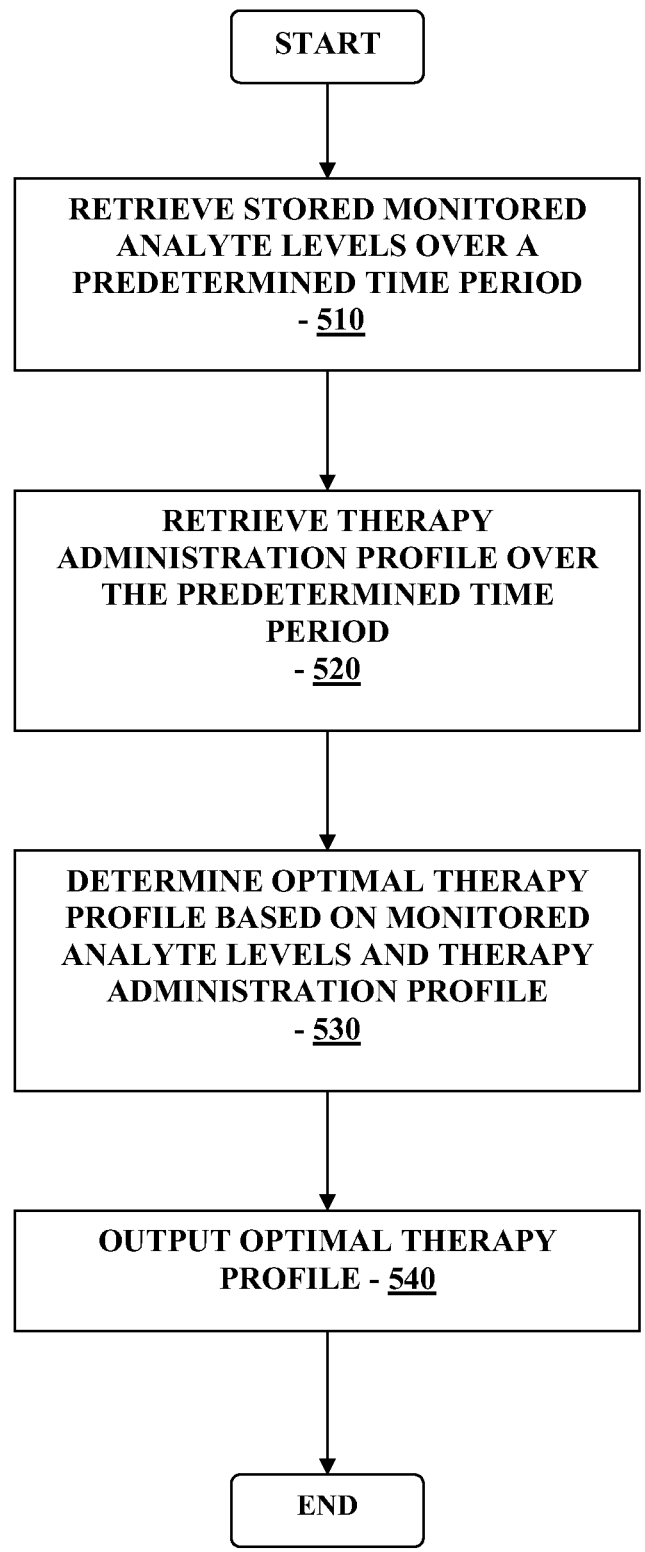
FIG. 5 is a flowchart illustrating therapy management related data processing in accordance with one embodiment of the present invention.

FIG. 5 is a flowchart illustrating therapy management related data processing in accordance with one embodiment of the present invention. Referring to FIG. 5, the stored monitored analyte levels over a predetermined time period is retrieved (510). Thereafter, the therapy administration profile over the predetermined time period is retrieved (520). For example, in one embodiment, the retrieved therapy administration profile may include one or more, but not limited to, stored basal profiles, carbohydrate and/or correction bolus amount administered, temporary basal profiles administered, and the like.

Referring again to FIG. 5, an optimal therapy profile is determined based on the retrieved monitored analyte levels and the therapy administration profile (530). Thereafter, the determined optimal therapy profile is output (540), for example, on the display unit 340 (FIG. 3) for review and/or further analysis by the patient, or the patient's healthcare provider. In this manner, in one embodiment of the present invention, it is possible to provide an automated pattern recognition for therapy administration profiles such as basal profiles and/or bolus amounts, to assist the healthcare providers in analyzing the monitored analyte levels in conjunction with the executed therapy administration profiles.

Figure 6:
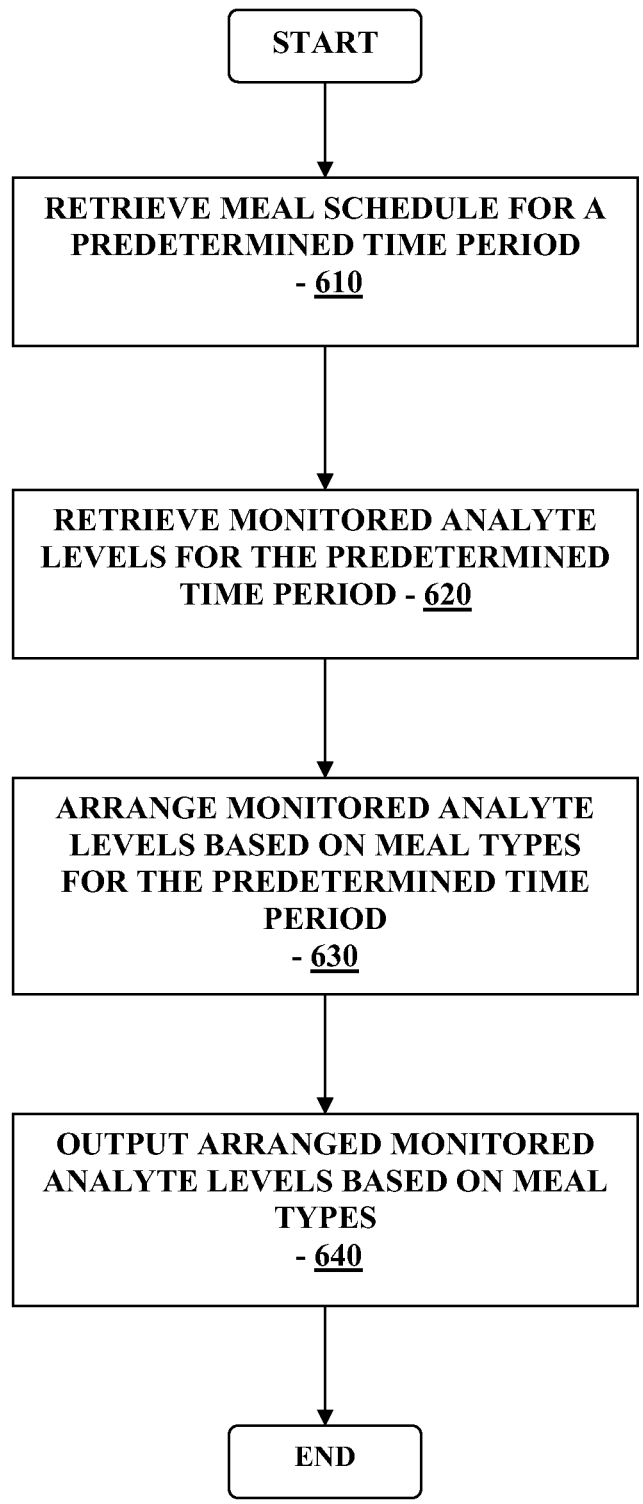
FIG. 6 is a flowchart illustrating time of day related data processing associated with meal events in accordance with one embodiment of the present invention.

FIG. 6 is a flowchart illustrating time of day related data processing associated with meal events in accordance with one embodiment of the present invention. Referring to FIG. 6, the meal schedule of the patient for a predetermined time period is retrieved (610). Thereafter, the monitored analyte levels for the predetermined time period is retrieved (620), for example, from the storage unit 320 (FIG. 3) of the remote terminal 140 (FIG. 1). Thereafter, the monitored analyte levels are arranged or realigned based on the meal types for the predetermined time period (630), and the arranged or realigned monitored analyte levels are output (640) on the display unit 340, for example.

That is, in one embodiment, based on the time of date information of a patient, and the associated monitored analyte levels of the patient, time based events may be associated with the corresponding monitored analyte levels. For example, for shift workers with irregular work schedule such as alternating day and night shifts, it would be possible to lineup meal events for such workers based on the time and date information and the associated monitored analyte levels so as to effectively and meaningfully perform data processing based on the intake of food and the monitored analyte levels.

A method in accordance with one embodiment of the present invention includes detecting a predetermined rate of increase in an analyte level of a patient over a predefined time period, and associating a temporal identifier associated with the detected predetermined rate of increase in the analyte level of the patient.

The predetermined rate of increase over a predefined time period may include a change in the analyte level exceeding a predetermined percentage over the predefined time period, where the predefined time period may include one of less than 5 minutes, less than 30 minutes, or less than one hour.

In another aspect, the predetermined percentage may include one of less than 15 percent, less than 50 percent, or less than 80 percent.

The method may also include storing the temporal identifier associated with the detected predetermined rate of increase in the analyte level of the patient.

The temporal identifier in one embodiment may include one or more of a time information or a date information.

In one aspect, the temporal identifier may include a meal event.

A method in accordance with another embodiment includes retrieving one or more stored analyte levels of a predetermined time period, retrieving one or more stored therapy administration profile for the predetermined time period, determining an optimal therapy profile based on the retrieved one or more stored analyte levels and the retrieved one or more stored therapy administration profile.

The method may include outputting the optimal therapy profile.

In one embodiment, the retrieved one or more stored therapy administration profile may include a pre-programmed one or more basal profiles.

In a further aspect, the predetermined time period may include one of a one day period, a 3 day period, or less than 8 day period.

The optimal therapy profile may include, in one embodiment, a modified one or more stored therapy administration profiles.

A method in accordance with yet another embodiment of the present invention includes retrieving a meal schedule for a predetermined time period, retrieving monitored analyte levels for the predetermined time period, and arranging the monitored analyte levels based on one or more meal types of the meal schedule for the predetermined time period.

The method may also include outputting the arranged monitored analyte levels.

The meal schedule in one embodiment may include one or more time period associated with breakfast, lunch or dinner.

In a further aspect, arranging the monitored analyte levels may include associating a respective analyte level for each retrieved meal schedule.

The predetermined time period in yet a further aspect may include one or more of a 3 day period, a seven day period, or less than 14 day period.

A system for providing diabetes management in accordance with still another embodiment includes a storage unit configured to store one or more data associated with monitored analyte levels, a processor unit operatively coupled to the storage unit, and configured to perform one or more processes to detect a predetermined rate of increase in an analyte level of a patient over a predefined time period, and associate a temporal identifier associated with the detected predetermined rate of increase in the analyte level of the patient.

The predetermined rate of increase over a predefined time period includes a change in the analyte level exceeding a predetermined percentage over the predefined time period.

The various processes described above including the processes performed by the processor 210 in the software application execution environment in the fluid delivery device 120 as well as any other suitable or similar processing units embodied in the analyte monitoring system 110 and the remote terminal 140, including the processes and routines described in conjunction with FIGS. 4-6, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or in a similar storage device in the analyte monitoring system 120 and in the storage unit 320 of the remote terminal 140 for execution by the processor unit 310) of the processor 210, may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method comprising:
   receiving, at one or more processors, analyte data from an analyte sensor;
   determining, using the one or more processors, an analyte level and a rate of change of the analyte level based on the received analyte data;
   automatically associating, using the one or more processors, a meal event with the determined rate of change of the analyte level when the determined rate of change exceeds a predetermined threshold level, wherein the meal event includes date and time information;
   storing the determined analyte level, the rate of change of the analyte level, and the meal event associated with the determined rate of change of the analyte level into a memory storage unit associated with the one or more processors;
   retrieving, using the one or more processors, from the memory storage unit a plurality of rate of change of analyte level data measured over a predetermined time period;
   determining, using the one or more processors, if a number of the retrieved plurality of rate of change of the analyte level data measured over the predetermined time period having the meal event associated therewith exceeds a predetermined number;
   retrieving, using the one or more processors, from the memory storage unit one or more stored medication administration profiles for the predetermined time period;
   the one or more processors utilizing an automated pattern recognition on the retrieved one or more stored medication administration profiles based on the retrieved plurality of rate of change of analyte level data measured over the predetermined time period; and
   determining, using the one or more processors, an optimal medication administration profile based on the retrieved plurality of rate of change of the analyte level data measured over the predetermined time period, the retrieved one or more stored medication administration profiles and the automated pattern recognition, when the number of the retrieved plurality of rate of change of the analyte level data measured over the predetermined time period having the meal event associated therewith exceeds the predetermined number.

2. The method of claim 1, further comprising outputting the optimal medication administration profile from an output unit.

3. The method of claim 1, wherein the retrieved one or more stored medication administration profiles includes a pre-programmed one or more basal profiles.

4. The method of claim 1, wherein the predetermined time period includes one of a one day period, a 3 day period, or less than an 8 day period.

5. The method of claim 1, wherein the optimal medication administration profile includes a modified one or more stored medication administration profiles.

6. The method of claim 1, wherein the predetermined time period comprises a week.

7. The method of claim 1, wherein the predetermined time period is based on replacement of one or more subcutaneous sensors.

* * * * *